United States Patent
Van Haarlem et al.

(10) Patent No.: US 9,291,583 B2
(45) Date of Patent: Mar. 22, 2016

(54) TRACE ELEMENT X-RAY FLOURESCENCE ANALYSER USING DUAL FOCUSING X-RAY MONOCHROMATORS

(71) Applicant: THE COMMONWEALTH OF AUSTRALIA COMMONWEALTH SCIENTIFIC AND INDUSTRIAL RESEARCH ORGANISATION, Campbell (AU)

(72) Inventors: Yves Leon Van Haarlem, Erskinville (AU); James Tickner, Meadows (AU)

(73) Assignee: THE COMMONWEALTH OF AUSTRALIA COMMONWEALTH SCIENTIFIC AND INDUSTRIAL RESEARCH ORGANISATION, Australian Capital Territory (AU)

( * ) Notice: Subject to any disclaimer, the term of this patent is extended or adjusted under 35 U.S.C. 154(b) by 253 days.

(21) Appl. No.: 13/957,803

(22) Filed: Aug. 2, 2013

(65) Prior Publication Data
US 2014/0037053 A1 Feb. 6, 2014

(30) Foreign Application Priority Data

Aug. 2, 2012 (GB) .................................. 1213789.9

(51) Int. Cl.
*G01N 23/223* (2006.01)
(52) U.S. Cl.
CPC ........ *G01N 23/223* (2013.01); *G01N 2223/076* (2013.01)
(58) Field of Classification Search
CPC .......... G01N 23/223; G01N 2223/076; G01N 2223/633; G01N 2223/652; G01N 23/2076
See application file for complete search history.

(56) References Cited

U.S. PATENT DOCUMENTS

| 4,599,741 A | 7/1986 | Wittry |
| 5,497,008 A * | 3/1996 | Kumakhov ............ B82Y 10/00 250/505.1 |

(Continued)

FOREIGN PATENT DOCUMENTS

| EP | 0 339 713 | 11/1989 |
| FR | 2 579 752 | 10/1986 |
| RU | 2 158 918 | 11/2000 |
| WO | WO 03/048745 | 6/2003 |

OTHER PUBLICATIONS

Grigorieva, I.G. et al., << HOPG as powerful x-ray optics >>, X-Ray Spectrometry, vol. 32, (2003), pp. 64-68.

(Continued)

*Primary Examiner* — Hoon Song
(74) *Attorney, Agent, or Firm* — Nixon & Vanderhye PC (57) ABSTRACT

An X-ray fluorescence analyzer is provided which comprises: (1) an X-ray source selected to produce an intense X-ray beam, (2) a first optical element that focuses the X-ray beam produced by the X-ray source onto a sample and selects X-rays of a desired energy, (3) an energy resolving detector, and (4) a second optical element that receives fluorescent X-rays emitted from elements in the sample and focuses a selected energy range of said fluorescent X-rays onto said energy resolving detector. Each of the first and second optical elements includes a crystal component. The X-ray fluorescence analyzer is configured such that: (i) the X-ray source has a spot size dimensioned so that it is substantially in a field of view of the first optical element, and (ii) the first optical element focuses the X-ray beam emitted by the X-ray source onto an area of the sample that corresponds to a field-of-view of the second optical element. Furthermore, the field of view for an optical element is defined as the area in the source plane of the respective crystal component over which X-rays are able to be emitted and still efficiently be reflected by said optical element.

18 Claims, 9 Drawing Sheets

(56) References Cited

U.S. PATENT DOCUMENTS

| | | |
|---|---|---|
| 6,754,304 B1 * | 6/2004 | Kumakhov .................. 378/45 |
| 2005/0157843 A1 * | 7/2005 | Chen et al. .................. 378/47 |
| 2007/0140420 A1 | 6/2007 | Radley et al. |

OTHER PUBLICATIONS

UK Search Report for GB Application No. 1213789.9, dated Oct. 31, 2012, (Dr. Stephen Otter).

* cited by examiner

TRACE ELEMENT X-RAY FLOURESCENCE ANALYSER USING DUAL FOCUSING X-RAY MONOCHROMATORS

CROSS-REFERENCE TO RELATED APPLICATIONS

The present application claims priority from British Patent Application No 1213789.9 filed on 2 Aug. 2012, the content of which is incorporated herein by reference.

TECHNICAL FIELD

This disclosure relates to an X-ray fluorescence analyser. In particular, the invention relates to an analyser which incorporates dual focusing monochromators. The analyser is particularly adapted to the detection of trace elements in bulk materials, such as slurries and dry powders as well as the on-stream analysis of trace high-value elements for minerals process monitoring, mining and exploration.

BACKGROUND

Existing X-ray analysers for bulk materials typically have detection limits of the order of a few tens of parts-per-million or larger, making such analysers unsuited to the measurement of valuable trace elements such as gold and platinum. Typically, valuable trace elements are mined at concentrations of a few parts-per-million or less and existing analysers are prone to interference due to scattered radiation or fluorescence emission from elements other than the element of interest.

X-ray focusing based on Bragg reflection at curved crystals allows collection of incident radiation over large solid angles and subsequent monochromatisation. By means of an appropriate curvature of the crystalline structure, efficient X-ray focusing becomes possible. By an appropriate variation of the Bragg reflection angle, it is possible to enhance the radiation in an energetic region of interest with respect to energetically undesirable parts of the spectrum.

Advances in Bragg diffraction materials offer significant potential as they enable analysers to combine selectivity with large effective solid angles. Highly Oriented Pyrolytic Graphite (HOPG)[1] is of particular interest and has been shown to be a very efficient X-ray monochromator. Optical elements having a boundary surface in the form of a curved surface are manufactured where the curved surface is formed from HOPG crystals. Perhaps the most distinguishing feature of HOPG crystals is a large mosaicity which leads to the largest integral reflectivity among all known crystals. Another feature of HOPG is that it can be formed into various shapes including an ellipse, a logarithmic spiral, a Johann geometry with singly bent (cylindrical) or doubly bent (spherical or toroidal) HOPG, or a Johansson geometry.

[1] Also referred to occasionally as highly annealed pyrolytic graphite (HAPG)

FR 2579752 describes the use of an analyser incorporating dual logarithmic spiral focusing elements. The disclosure reports detection limits of 0.05-0.1 parts-per-million for elements in solution, which would be equivalent to approximately 0.8-2.0 parts-per-million for elements in a slurry. However, such an analyser is unsuited to the measurement of valuable trace elements such as gold and platinum.

It is desired to develop an analyser which is capable of yielding improvements in its detection limit compared to the results reported previously.

SUMMARY

An X-ray fluorescence analyser is provided comprising:
an X-ray source selected to produce an intense X-ray beam;
a first optical element that focuses the X-ray beam produced by the X-ray source onto a sample and selects X-rays of a desired energy;
an energy resolving detector; and
a second optical element that receives fluorescent X-rays emitted from elements in the sample and focuses a selected energy range of said fluorescent X-rays onto said energy resolving detector;
wherein each of the first and second optical elements includes a crystal component, and wherein the X-ray fluorescence analyser is configured such that:
(i) the X-ray source has a spot size dimensioned so that it is substantially in a field of view of the first optical element, and
(ii) the first optical element focuses the X-ray beam emitted by the X-ray source onto an area of the sample that corresponds to a field-of-view of the second optical element;
wherein the field of view for an optical element is defined as the area in the source plane of the respective crystal component over which X-rays are able to be emitted and still be efficiently reflected by said optical element.

The X-ray fluorescence analyser may further be configured such that the second optical element focuses the selected energy range of said fluorescent X-rays onto an area that corresponds to the size of an active area of the energy resolving detector.

Figure 3:
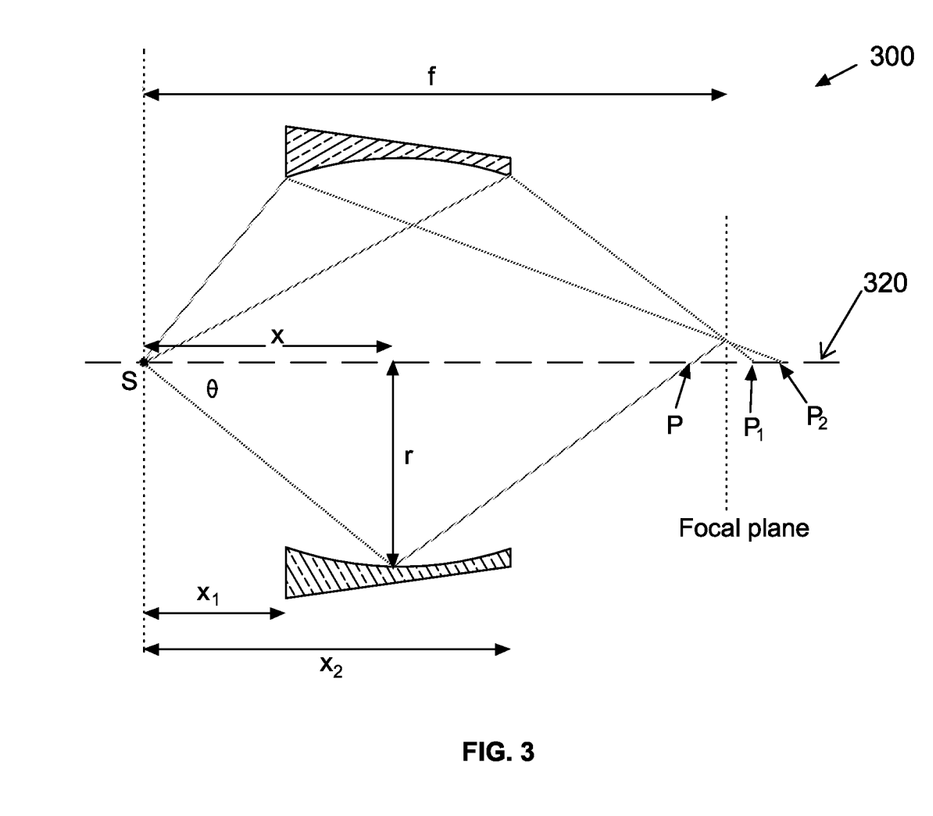
FIG. 3 is a schematic diagram of the crystal component of an optical element used in the X-ray fluorescence analyser shown in FIG. 1, that also serves to define the terms and dimensions used.

The crystal components of both optical elements may have the form of portion of a logarithmic spiral of revolution with a parametric form $x = A \cos \theta e^{-b\theta}$, $r = A \sin \theta e^{-b\theta}$; wherein A and b are constants, x measures distance along the axis of revolution, r is the radius of the spiral with respect to this axis and $\theta$ is the polar angle measured with respect to the axis of revolution (see FIG. 3).

The parameters describing the shape of the logarithmic spiral for the second optical element are A, b, $x_1$ and $x_2$ where $x_1$ and $x_2$ are the limits of the portion of the logarithmic spiral forming the optical element. The values of these parameters are determined by:

(a) calculating A and b using equations $$\theta_b = \sin^{-1}\left(\frac{6.199}{E*d}\right),$$

$$b = \frac{1}{\tan\theta_b}$$

and $$A = \frac{\frac{1}{2}sf\exp(-b\theta_b)}{\cos(\theta_b)};$$

wherein s is an arbitrary focal shift parameter between 0 and 1, d is a lattice spacing of the crystal component, E is the energy of the fluorescent X-ray to be focused by the element and f is a desired focal length of the crystal component, equal to the distance from a surface of the sample to a surface of the detector;

(b) calculating the radius R in the focal plane of the X-ray beam focused by the crystal component using the equation $R = |r - (f-x)\tan(2\theta_b - \theta)|$; and (c) identifying values $x_1$ and $x_2$ that correspond to the range of x values over which R is less than the radius of the X-ray detector.

Steps (a), (b) and (c) may be repeated for different values of f and s to identify the design of the crystal component that subtends the largest solid angle at the sample, whilst simultaneously having the smallest size that can be physically manufactured.

The field of view of the second optical element may be estimated using a numerical integration or stochastic estimation procedure. A non limiting example of a stochastic estimation procedure is Monte Carlo estimation.

The crystal component of the first optical element may be designed such that it produces a focal spot matching the field of view of the second optical element. Accordingly, the crystal component of the first optical element may have the form of a logarithmic spiral of revolution similar to the one described above for the second optical element, where the form of the spiral is described by a separate set of parameters A, b, $x_1$ and $x_2$ which are determined by:

(a) calculating A and b using equations $$\theta_b = \sin^{-1}\left(\frac{6.199}{E*d}\right),$$

$$b = \frac{1}{\tan\theta_b}$$

and $$A = \frac{\frac{1}{2}sf\exp(-b\theta_b)}{\cos(\theta_b)};$$

where s is an arbitrary focal shift parameter between 0 and 1, d is a lattice spacing of the crystal, E is the characteristic X-ray energy emitted by the source that is to be focused by the optical element and f is the focal length of the crystal component, equal to the distance from the source emission point to the surface of the sample; and (b) calculating the radius R in the focal plane of the X-ray beam focused by the crystal component using the equation $R=|r-(f-x)\tan(2\theta_b-\theta)|$, and (c) identifying values $x_1$ and $x_2$ that correspond to the range of x values over which R is less than the radius of field of view of the second optical element.

Steps (a), (b) and (c) may be repeated for different values of f and s to identify the design of the crystal component that subtends the largest solid angle at the X-ray source emission point, whilst simultaneously having the smallest size that can be physically manufactured and positioned with respect to the X-ray source.

Each of the first and second optical elements may comprise a machined metal or plastic substrate coated in the crystal component. The crystal component of the first and second optical elements is preferably highly-oriented pyrolytic graphite (HOPG). The crystal component may be a 100 μm to 500 μm thick layer of HOPG. The substrate has the form of a cylinder or tapered cylinder (frustum) with an inner machined cavity having the form of a logarithmic spiral of revolution.

Preferably the X-ray source is selected to emit an X-ray beam from a region smaller than the field of view of the first optical element.

The X-ray source may be selected to have a spot size having a diameter of ≤1 mm, preferably ≤0.5 mm, and more preferably ≤50 μm.

The X-ray source may be an X-ray tube having an X-ray target and operable to produce an intense emission of characteristic X-rays resulting from fluorescent X-rays superimposed on the Bremsstrahlung spectrum.

The X-ray target may be (without being limited to) one of a Molybdenum target, a Copper target, a Rhodium target, a Palladium target, a Silver target, a Gold target, or a Tungsten target. In an embodiment using a Molybdenum target, the X-ray tube may be operated at voltages between 25-100 kV and preferably around 50-90 kV to produce intense 17.4 keV Mo K-alpha X-rays. In an embodiment using a Copper target the X-ray tube may be operated at voltages between 15-60 kV to produce intense 8.0 keV Cu K-alpha X-rays.

The X-ray fluorescence analyser may further comprise a support structure to rigidly hold at least the first optical element, the second optical element and the energy resolving detector in relation to one another. The support structure may be in the form of a machined metal block.

The X-ray fluorescence analyser may further comprise mounting means for mounting the X-ray source and bringing the X-ray source into correct alignment with the support structure. The mounting means may comprise translation stages that provide at least transverse motion in two axes and preferably 3-dimensional translation.

In certain embodiments, the X-ray fluorescence analyser may comprise two or more energy resolving detectors each with an associated second optical element. The respective second optical elements may be identical or of different designs. For example, in one embodiment, the analyser comprises two detectors each having an associated second optical element, where each of the second optical elements are tuned to the same X-ray energies. The effect of this is that the count rate for any particular trace element doubles which leads to an improvement in measurement accuracy achievable for a given measurement duration. In another embodiment, the analyser comprises two second optical elements tuned to different X-ray energies in order to detect fluorescent X-rays from different trace elements.

The energy resolving X-ray detector(s) may be Si PIN or Si drift devices, where the active diameter of the detector is about 3 to 8 mm.

Each of the energy resolving X-ray detectors preferably include processing electronics adapted to process output signals obtained from the respective detector.

BRIEF DESCRIPTION OF THE DRAWINGS

Non-limiting example(s) will now be described with reference to the accompanying drawings, in which.

DETAILED DESCRIPTION

Whilst the example described in the detailed description to follow is in relation to the on-stream analysis of trace high-value elements for minerals process monitoring, mining and exploration, it should be appreciated that the invention may also be applied for the real-time monitoring of toxic elements or environmentally damaging elements in water and/or waste treatment plants. Further still, the invention may be used for portable in-field analysis of mineral samples.

Figure 1:
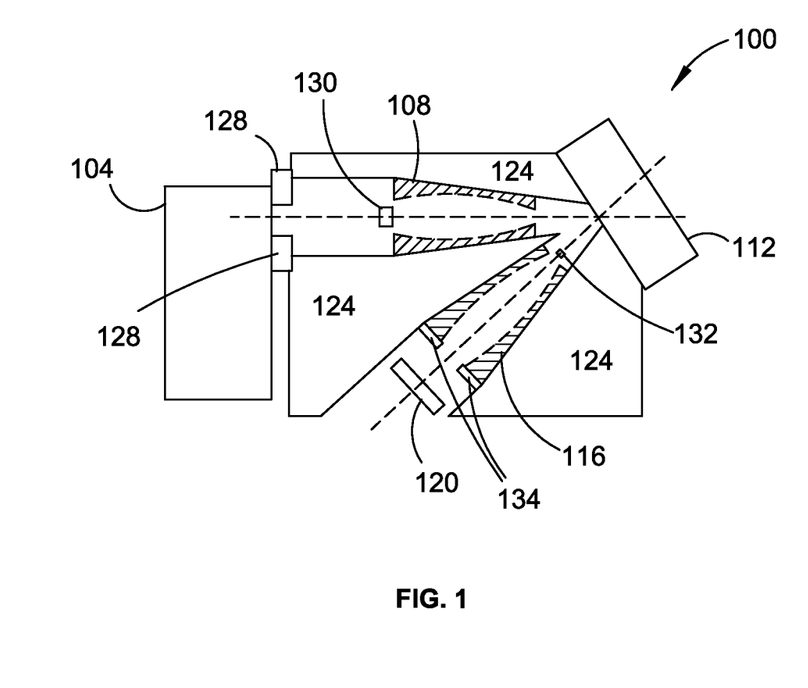
FIG. 1 is a schematic diagram of an X-ray fluorescence analyser in accordance with one embodiment of the invention.

Referring first to FIG. 1, a schematic diagram of the X-ray fluorescence analyser 100 in accordance with one embodiment of the invention is illustrated. Note that the relative placement of each of the components is not to scale. In this example, the X-ray fluorescence analyser 100 is designed to determine the concentration of gold tailings present in a quantity of slurry.

The X-ray fluorescence analyser 100 includes an X-ray source 104, a first optical element in the form of a first focusing monochromator 108, a sample presentation means 112, a second optical element in the form of a second focusing monochromator 116 and an energy resolving detector 120 in the form of a silicon drift detector. The analyser 100 also includes a support structure 124 in the form of a machined metal block that rigidly holds the first focusing monochromator 108, the second focusing monochromator 116, the energy resolving detector 120 and the sample presentation means 112 in relation to one another, and mounting means 128 for mounting the X-ray source 104 and bringing the X-ray source 104 into alignment with respect to the support structure. Use of the support structure 124 greatly simplifies setup and alignment and makes for a more robust implementation in industrial environments.

A first blocking means 130 is further provided to block transmission of a direct beam of X-rays reaching the sample 112. Similarly, a second blocking means 132 is provided to block transmission of a direct beam of fluorescent and scattered X-rays from the sample 112 reaching the energy resolving detector 120. Each of the first and second blocking means are supported on thin polymer sheets. An outer collimator ring 134 is further provided and situated in front of the energy resolving detector 120.

The sample presentation means 112 is configured depending on the application. The sample presentation means 112 may comprise a thin polymer window behind which is conveyed a continually flowing liquid or slurry or a continually moving bed of powder or dry material. In other embodiments the sample presentation means may comprise a sample stage upon which a discrete sample of material may be positioned.

It should be appreciated that the X-ray source 104 is selected, depending on the element or elements in the sample which are to be detected. In this example, the X-ray source is in the form of a micro-focus tube in which electrons detached from a cathode are accelerated by an electric field and hit the target, which in this example is a Molybdenum (Mo) target, and where they lose their kinetic energy in various interaction processes with the atoms of the anode material. One result of these interaction processes is the generation of X-rays, the spectrum of which comprises both a continuous part (known as Bremsstrahlung) and some prominent peaks, known as characteristic X-rays. The spectral distribution and intensity of the Bremsstrahlung part is proportional to both the acceleration voltage and the atomic ordinal number of the target material. Higher acceleration voltages and heavier anode materials increase the intensity of the continuous spectrum part at higher energies.

The X-ray source 104 is operable at voltages of between 30 keV and 50 keV in order to produce characteristic Mo K-alpha X-rays having an energy of 17.4 keV. The micro-focus tube is configured such that the source spot size of this micro-focus tube has a diameter of <50 µm. This ensures that X-rays emitted from the X-ray tube 104 have the highest possible probability of passing through the first focusing monochromator 108.

For detection of gold tailings in a sample, configuring the X-ray source 104 to have Molybdenum as a target and producing 17.4 keV characteristic X-rays resulting from fluorescent X-rays on top of the Bremsstrahlung spectrum, is a good choice. To be effective, the best X-ray energy to use is one that lies sufficiently above the excitation threshold for the element of interest to ensure that X-rays scattered elastically and inelastically in the sample do not overlap the fluorescent line of the element of interest. At the same time, the excitation energy should not lie too far above the excitation threshold for the element of interest, as the efficiency of excitation of the fluorescence process decreases with increasing excitation energy. In this example, the excitation thresholds for gold L X-rays lie in the range 11.9-14.4 keV and the fluorescent peak of interest lies at 11.4 keV. X-rays of 17.4 keV can efficiently excite gold fluorescence, and elastically and inelastically scattered X-rays of this energy predominantly have energies above 14 keV, leading to minimal overlap with the gold fluorescence lines.

The X-ray source 104 mounts to the support structure 124 via translation stages (not shown) that provide motion in three orthogonal axes. This is advantageous because the X-ray focus spot position in the tube varies significantly from tube to tube, making realignment important when the tube is moved or replaced.

The first focusing monochromator 108 and the second focusing monochromator 116 are each formed from a machined aluminium substrate coated in a 100 µm to 500 µm thick layer of highly oriented pyrolytic graphite (HOPG). For each monochromator, their respective surface is generated by taking a 2-dimension curve in the shape of a logarithmic spiral and then rotating this curve about its axis to produce a rotationally symmetric, 3-dimensional surface. The substrate has the form of a cylinder or frustum, with an inner machined cavity having the form of a logarithmic spiral of revolution.

Generally speaking, the HOPG is formed into shape using known techniques such as those described by I. G. Grigorieva and A. A. Antonov in "HOPG as a powerful X-ray Optic", X-Ray Spectrometry, X-Ray Spectrum. (2003); 32: 64-68, the details of which are incorporated herein by reference.

When designing an X-ray fluorescence analyser for trace element detection, efficiency is very important. That is, as large a fraction as possible of the X-rays emitted from the X-ray source need to be focused on to the sample and as large a fraction as possible of the fluorescent X-rays emitted from the sample needs to be focused back on to the detector. At the same time, it is necessary to minimise the number of X-rays of the wrong energy (either unwanted X-rays from the source, or unwanted background X-rays scattered from the sample) being transmitted through the optical elements.

The difficulty in designing the optical elements is that there is no curve which simultaneously meets the Bragg condition (that is X-rays emitted from a point hit the surface at a constant angle) and that focuses reflected X-rays back to a single point. Whilst several options exist, each is compromised. One option is an optical element having a crystal component whose boundary surface takes the form of a logarithmic spiral where the focus at a source point 'S' meets the Bragg condition. However with this arrangement, the optical element is unable to focus emitted X-rays to a single point. A second option is an optical element having a crystal component whose boundary surface is formed having a Johann geometry. The Johann geometry describes the situation where the crystal component has the form of part of the arc of a circle. This design is favourable because of the relative ease of bending crystals into circular curves. However, this design rapidly deviates from meeting the Bragg condition. A third option is an optical element having a crystal component whose boundary surface takes the form of an ellipse having the source point at one focus. Such an optical element will focus all rays to a point positioned at its second focus, however the reflection angle will not be constant. A fourth option is the Johansson geometry which advantageously satisfies both the Bragg and focusing conditions. However, this arrangement requires that the crystal planes of the HOPG layer be no longer parallel to the underlying substrate and such a crystal is not able to be manufactured according to modern techniques. Approximations to a Johansson geometry have been reported in the literature by making the surface of the monochromator a series of steps, with abrupt changes in radius. However, incorporating this approximation significantly complicates the manufacture of the optical element.

Figure 2:
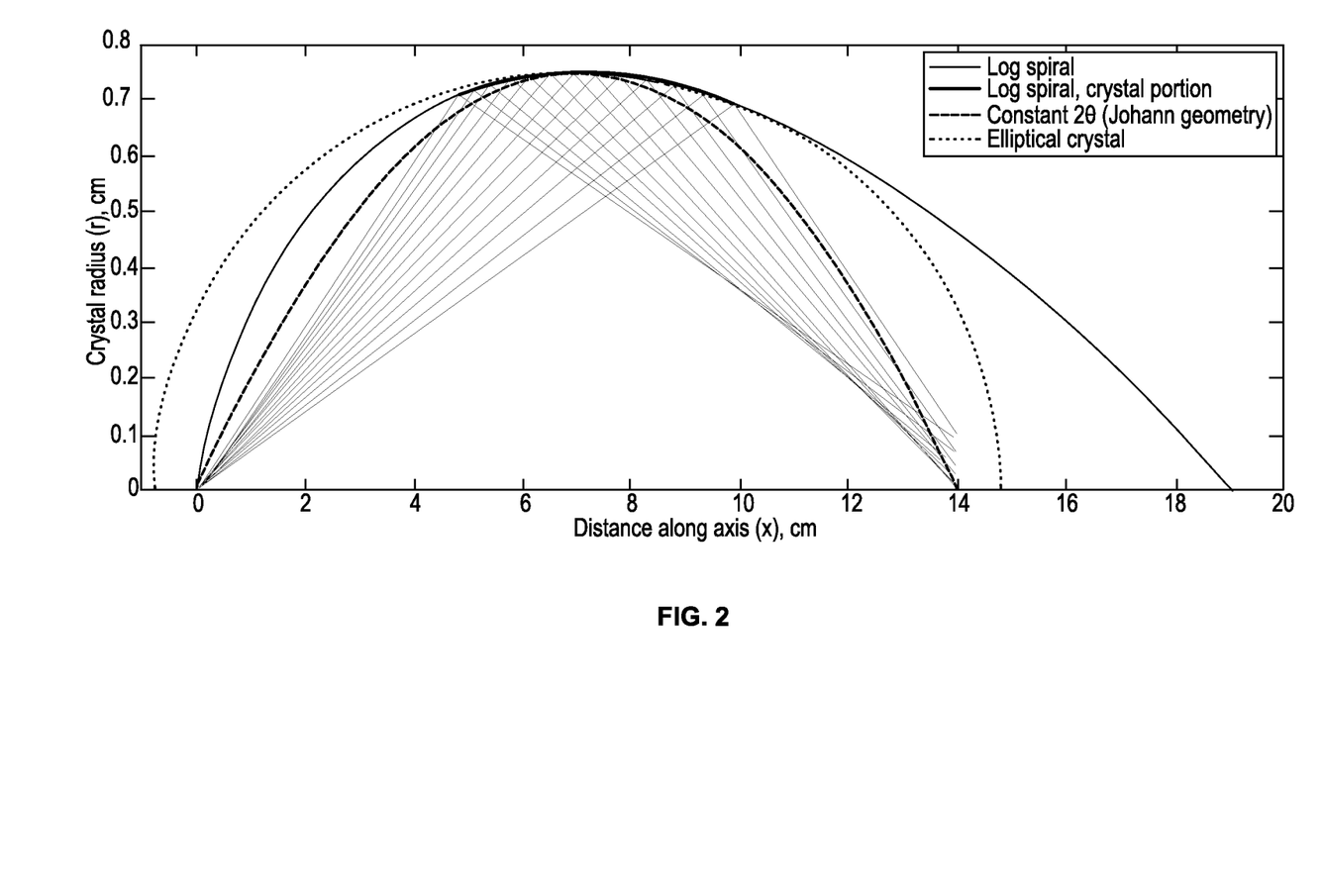
FIG. 2 is a graph showing three optical elements designed to reflect 17.4 keV X-rays, each having a different crystal shape.

FIG. 2 illustrates three of the choices for the geometry of the crystal component; the logarithmic spiral, Johann and elliptical geometries. It can be seen that all three curves coincide at the midpoint between the source point and focal plane. At this midpoint, the X-ray emission angle $\theta=\theta_b$. The 'rays' depict X-rays emitted from a point source being reflected from a portion of the logarithmic spiral; note how these X-rays are not all brought to the same focal point. It can be seen that when we move away from $\theta=\theta_b$, X-rays hit the Johann and elliptical curves at angles that increasingly differ from the Bragg angle $\theta_b$, meaning that reflection will not occur for X-rays of the desired energy. This is especially true for the traditional Johann geometry.

The inventors have selected the logarithmic spiral shape and assert that satisfying the Bragg condition is essential for reflecting X-rays of a particular energy. How the inventors handle the problem of imperfect focusing is described below.

FIG. 3 is a schematic diagram of a basic design of an optical element 300. As stated above, the optical element 300 is composed of a substrate coated with a crystal component. The substrate is an inert aluminium substrate whilst the crystal component is a thin (between 0.1 and 0.5 mm) layer of HOPG. The crystal component of the optical element 300 has the form of a surface of revolution about an axis, as indicated by the dashed line 320. The logarithmic spiral curve centered on a point S (the origin) is defined parametrically by $x=A \cos\theta e^{-b\theta}$, $r=A \sin\theta e^{-b\theta}$ where $\theta$ is the polar angle measured from a chosen axis, x is the distance from the origin measured along this axis and r is the radius of the spiral. The unique property of the logarithmic spiral is that the angle between a line connecting the origin S to a point on the curve, and the tangent at that point, has a constant value given by the relation $$\tan^{-1} = \left(\frac{1}{b}\right).$$

The inventors have ascertained that when designing a monochromator for X-rays, the angle between the incident X-rays and the tangent should be made equal to the Bragg diffraction angle, leading to the relation $$b = \frac{1}{\tan\theta_b}$$

where the Bragg angle $$\theta_b = \sin^{-1}\left(\frac{6.199}{E*d}\right)$$

where E is the X-ray energy in keV and d is the HOPG crystal spacing in Angstroms. For the energies of interest to this application, typically 10-20 keV, the Bragg angle is within the range 10.6°-5.3°. For example, to monochromate the 17.4 keV K-alpha X-rays from a Mo-target X-ray tube using a HOPG crystal (d=3.356 A), $\theta_b$=6.1° and b=9.38.

As stated above, the logarithmic spiral is strictly speaking not a focusing curve. The consequence of this is that X-rays emitted from the source S, hitting different parts of the crystal, recross the axis at different distances from the source. The X-rays hitting the part of the curve that is parallel to the axis (indicated at an angle $\theta$ in FIG. 3) are focused at the shortest distance, given by the relation $$2Ae^{\left(\frac{\theta_b}{\tan\theta_b}\right)} * \cos\theta_b.$$

Rays making angles greater or less than $\theta$ with the axis are focused at longer distances. In other words, there is no curve which simultaneously meets the Bragg condition and that focuses reflected rays back to a single point P.

To a good approximation, the X-ray source 104 can be treated as a point source. However, due to the poor focusing of the log spiral curve, this will produce an X-ray 'spot' on the sample 112 of a finite size. The size of this spot is important when considering the effectiveness of the second focusing monochromator 116 which is situated between the sample 112 and the energy resolving detector 120. The log spiral is only a good reflector from X-rays emitted on its axis. Consequently, if the illuminated X-ray spot on the sample 112 is too large, the induced fluorescent X-rays that are produced a long way from the axis of the second focusing monochromator 116 will not be reflected and will fail to reach the energy resolving detector 120.

Field of View

To design the optical elements, the inventors have developed a concept termed 'field of view'. As should be appreciated, an optical element designed to efficiently focus X-rays of a chosen energy emitted from a point on the axis of the optical element, will be less efficient at focusing X-rays of the same energy emitted from an off-axis point. In general, the further off-axis the emission point moves, the lower the reflection efficiency for the desired X-rays.

Therefore, the 'field of view' for an optical element is defined as the area in the source plane over which X-rays are able to be emitted and still efficiently be reflected by the optical element.

Designing an online X-ray fluorescence analyser for the measurement of trace elements then requires that the following two conditions are met:

(1) the X-ray source has a spot size dimensioned so that it is substantially in a field of view of the first focusing monochromator, (or in other words, X-rays emitted from the X-ray source are mostly emitted in the field of view of the first focusing monochromator); and
(2) the first focusing monochromator focuses X-rays onto an area of the sample that corresponds to the field-of-view of the second focusing monochromator.

In order to further optimise the analyser it is preferable to include a third condition, namely that:

(3) the second focusing monochromator focuses X-rays onto an area that corresponds to the size of the detector.

The field-of-view of an optical element depends on the shape of the optic surface, the thickness of the HOPG layer and the mosaicity of the HOPG layer. The layer does not comprise a single crystal, but rather a mosaic of individual crystals with slightly different orientations. Typically, the distribution of the crystallite normals about the mean surface normal has a full-width-half-maximum (FHWM) of about 0.3°-0.5°.

Figure 4:
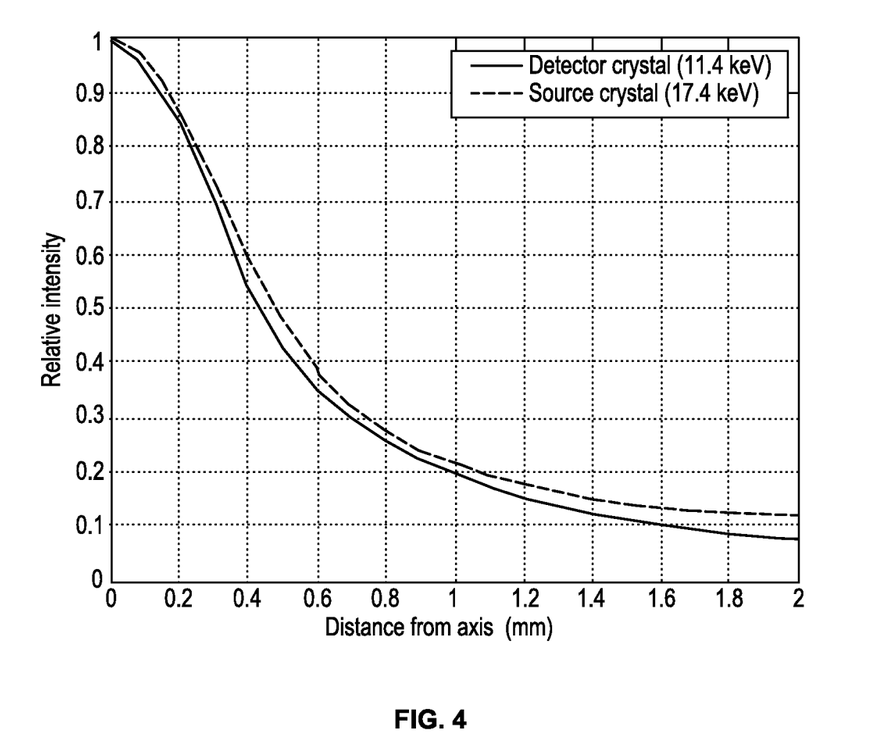
FIG. 4 is a graph showing the relative transmission efficiency of optical elements as a function of distance of the source point from the element axis.

It is not possible to analytically calculate the field-of-view including all these effects, however results of a simple numerical integration for two typical crystal designs are shown in FIG. 4. Specifically, this plot shows the relative reflection efficiency as a function of distance from axis for a crystal designed to focus 11.4 keV (gold fluorescence) X-rays; very similar results are obtained for a crystal design to focus 17.4 keV (Mo fluorescence) X-rays.

Accordingly, the X-ray source spot size should have a diameter <1 mm. A diameter <0.4 mm is preferable to ensure that the X-ray beam emitted from the X-ray source has the highest possible probability of passing through the first optical element. In the inventors' preferred embodiment a microfocus tube with a spot-size of <50 μm is used, so this condition is easily met.

It is critical that the first focusing monochromator focuses X-rays onto an area of the sample that corresponds to the field-of-view of the second focusing monochromator. If the first focusing monochromator focuses X-rays outside of the field-of-view of the second focusing monochromator, then any fluorescence that those rays that impinge outside of the field-of-view of the second focusing monochromator(s) induce is highly unlikely to be transmitted through the second focusing monochromator(s) and onto the energy resolving detector(s), and will result in increased levels of background noise which will degrade the accuracy of the analyser.

Again referring to FIG. 3, and in order to design each of the optical elements, the following design parameters apply:

x=the distance along the crystal axis from the source plane where an incident X-ray hits the crystal;
r=the radius of the crystal at a distance x from the source plane;
A=a constant that governs the size or scale of the logarithmic spiral, decreasing A shifts the focal plane slightly further from the source point;
b=a constant that governs the 'tightness' of the logarithmic spiral;
θ=the polar angle measured from the crystal axis;
f=the focal length of the crystal, defined as the shortest distance from the source point at which rays reflected from the crystal can be refocused;
S=the source point;
D=the focal distance, i.e. the distance at which rays emitted from the source point at an angle theta to the crystal axis are focused (for a logarithmic spiral defined by parameters A and b);
R=the focal radius, i.e. the radius of a ring into which X-rays incident at an angle θ to the crystal axis are focused. This is in relation to a plane whose normal is parallel to the crystal axis and that lies at the focal distance f from the source point S.

The following explains how the HOPG crystal component of the optical element can be designed to meet these requirements, using the first optical element as an example.

Firstly, consider a logarithmic spiral with parametric form:

$$x = A \cos\theta e^{-b\theta}, r = A \sin\theta e^{-b\theta} \qquad (2)$$

For the Bragg condition to be satisfied we need:

$$b = \frac{1}{\tan\theta_b} \qquad (3)$$

The focal length of the crystal is defined to be shortest distance from the source point at which rays reflected from the crystal can be refocused. The parameter A is related to the focal length via equation (4):

$$A = \frac{\frac{1}{2} f \exp(-b\theta_b)}{\cos(\theta_b)} \qquad (4)$$

For a logarithmic spiral defined by parameters A and b, rays emitted from the source point at an angle θ to the crystal axis are focused at a distance D given by equation (5):

$$D = x + \frac{r}{\tan(2\theta_b - \theta)} \qquad (5)$$

where x and r are given by equations (2). Note that when θ=θ_b, equation (5) reduces to D=f as expected.

In a plane whose normal is parallel to the crystal axis and that lies at the focal distance f from the source point 'S', X-rays incident at an angle θ to the crystal axis are focused into a ring of radius R given by:

$$R = |r - (f - x)\tan(2\theta_b - \theta)| \qquad (6)$$

When θ=θ_b, equation (6) reduces to R=0, as expected.

Figure 5A:
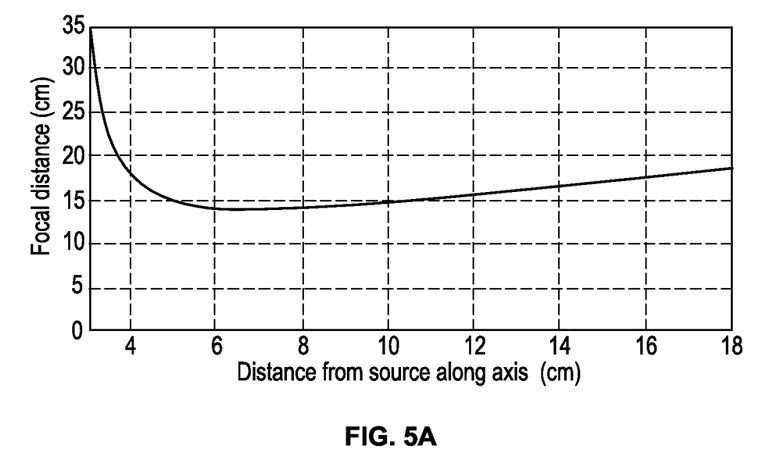
FIG. 5A is a graph showing the focal distance D as a function of distance along the source axis where the X-ray hits the surface of the crystal component of the optical element.
Figure 5B:
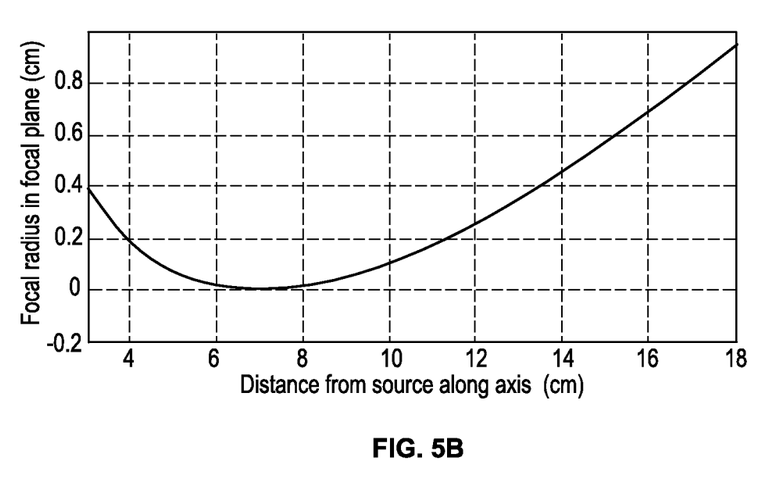
FIG. 5B is a graph showing the focal radius R as a function of distance along the source axis where the X-ray hits the surface of the crystal component of the optical element.

FIGS. 5A and 5B respectively plot the focal distance D, and focal radius in the focal plane R, as a function of distance along the crystal axis x, for a crystal with a focal length f of 14 cm designed to focus 17.4 keV X-rays. The minimum focal distance (f=14 cm) occurs at the midpoint between the source point and focal plane, which corresponds to the widest part of the crystal where the crystal surface is parallel to the crystal axis; at this point, θ=θ_b. For X-rays emitted at larger or smaller angles, the focal point lies beyond the focal plane, and in the focal plane itself X-rays are focused to a ring with a non-zero radius R.

Requiring X-rays to be focused to a spot with a certain maximum diameter imposes limits on the portion of the logarithmic spiral that can be used. If an optical element is used which extends beyond these limits, a portion of the X-rays hitting the crystal component of the optical element will be reflected outside of the desired spot.

Optimum performance is also achieved when the sample 112 and energy resolving detector 120 are positioned slightly beyond the minimum focal distance P (FIG. 3). Working at a slightly longer distance offers the best compromise in average focal length and reduces the size of the focal spot.

This change is effected by introducing a focal-shift parameter s into the calculation of A, replacing equation (4) with $$A = \frac{\frac{1}{2} sf \exp(-b\theta_b)}{\cos(\theta_b)} \quad (7)$$

Figure 6:
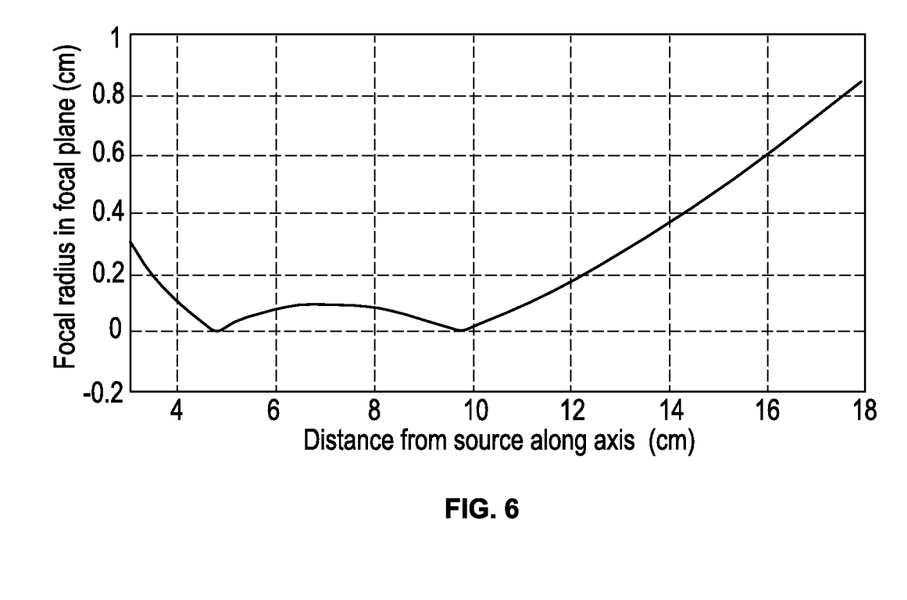
FIG. 6 is a graph showing the focal radius in focal plane R for the case where the focal plane is shifted slightly beyond the minimum focal distance f.

FIG. 6 shows the effect of this change. X-rays are now focused into a given diameter spot over a longer length of optical element. This means that the optical element subtends a larger solid angle at the source spot, so that an increasing fraction of X-rays emitted from the source spot have a chance of being reflected by the optical element.

The portion of the logarithmic spiral to use for the optical element can now be determined straightforwardly by inspection of FIG. 5. If a source spot of some maximum diameter is required, then the portion of the optical element with R less than one half of this diameter should be chosen. For example, for the optical element presented here and a target focal spot diameter of 0.2 cm, the crystal should be formed from the portion of curve lying between approximately x=4.0 and x=11.0 cm.

The only remaining free parameter in the design of the crystal component of the optical element is the focal distance f. Several factors serve to constrain the choice of this parameter:

(i) Larger values of f mean that a larger optical element is required to accept X-rays over the same range of angles. The cost of crystal manufacture scales approximately like the area of the deposited HOPG layer, meaning that the cost scales like $f^2$. This indicates that the smallest possible value of f should be chosen.

(ii) For any choice of X-ray source, there is some minimum distance from the spot from which X-rays are emitted at which it is possible to place an optical element. For example, it is common for X-rays to be emitted from a point which lies on the axis of the X-ray source, meaning that the crystal component cannot be placed any closer to this point than the outer radius of the X-ray source. Typically, this distance may vary from <1 mm to several cm. Too small a choice for f may mean that the crystal needs to be placed closer to the X-ray emission point than is physically possible.

(iii) There is a minimum radius of curvature with which HOPG crystals can be manufactured. Using current fabrication processes, this minimum radius is approximately 4-5 mm. If the radius of the crystal at any point is less than this minimum, then a larger value of f needs to be chosen.

Given consideration (i), f is chosen to have the smallest value consistent with considerations (ii) and (iii).

The process for selecting the parameters for the logarithmic spiral is therefore as follows:

1. Determine the desired size of the focal spot of the optical element. For the source crystal, this should correspond to the field-of-view of the detector crystal (approximately 2 mm diameter for our case).

2. Estimate the focal length f; an initial guess is sufficient at this stage, and this can be refined. Typical values for X-rays in the energy range 10-20 keV are 10-20 cm.

3. Calculate the spiral parameters A and b using equations (1), (3) and (7). Assume an initial value of s=1.0.

4. Use equations (2) and (6) to calculate the focal radius in the focal plane, R.

5. Repeat steps 3-4, iteratively reducing the value of parameter s until the focal radius in the focal plane at angle $\theta=\theta_b$ is equal to the desired radius of the focal spot (FIG. 5), and the angular acceptance of the crystal element is maximised.

6. Determine the portion of the logarithmic spiral over which reflected X-rays hit the focal plane within the desired radius of the focal spot.

7. Determine the minimum radius of the spiral over this portion of the curve. If the minimum radius is greater (less) than the minimum radius which can be manufactured, or if the distance from the source point to the start of the crystal is larger (smaller) than the minimum physically possible distance, then decrease (increase) the value of the focal length f and repeat from step 2.

Whilst the iterative steps can be automated, the inventors have found that in practice that the process requires very few attempts to converge to a satisfactory solution. Therefore, in most cases a manual iterative process is entirely adequate.

Ideally, the detector crystal should be designed first. It should be designed to focus X-rays into an area corresponding to the size of the X-ray detector to be used. The field-of-view of this crystal can then be estimated using a numerical integration or stochastic (Monte Carlo) estimation procedure. The source crystal can then be designed to produce a focal spot matching the desired field-of-view. An X-ray source emitting X-rays from a region smaller than the field-of-view of the source crystal should be selected.

Table 1 summarises the design parameters selected for a specific case, an X-ray fluorescence analyser designed to measure gold. A Mo-target X-ray tube is used and the source crystal is designed to focus the 17.4 keV Mo K-alpha X-rays onto the sample. The gold in the sample is detected via its 11.4 keV fluorescent X-rays. A detector diameter of 6 mm is assumed.

TABLE 1

Design parameters for the crystal component used for an analyser configured to detect gold

| Parameter | Source crystal | Detector crystal |
|---|---|---|
| X-ray energy (keV) | 17.4 | 11.4 |
| Bragg angle | 6.08° | 9.28° |
| Focal spot radius (mm) | 1.0 | 3.0 |
| f (cm) | 14.0 | 10.0 |
| A (cm) | 17.9 | 11.7 |
| b | 9.38 | 6.12 |
| s | 0.94 | 0.86 |
| Min. dist from source/sample (cm) | 4.0 | 2.0 |
| Crystal length (cm) | 5.85 | 5.9 |
| Min. crystal radius (mm) | 6.5 | 5.3 |

It is envisaged that embodiments of the invention will allow detection limits significantly below 0.1 parts-per-million to be achieved for trace elements such as gold and platinum, whilst simultaneously significantly reducing the power consumption, size, cost and complexity of the analyser.

Figure 7A:
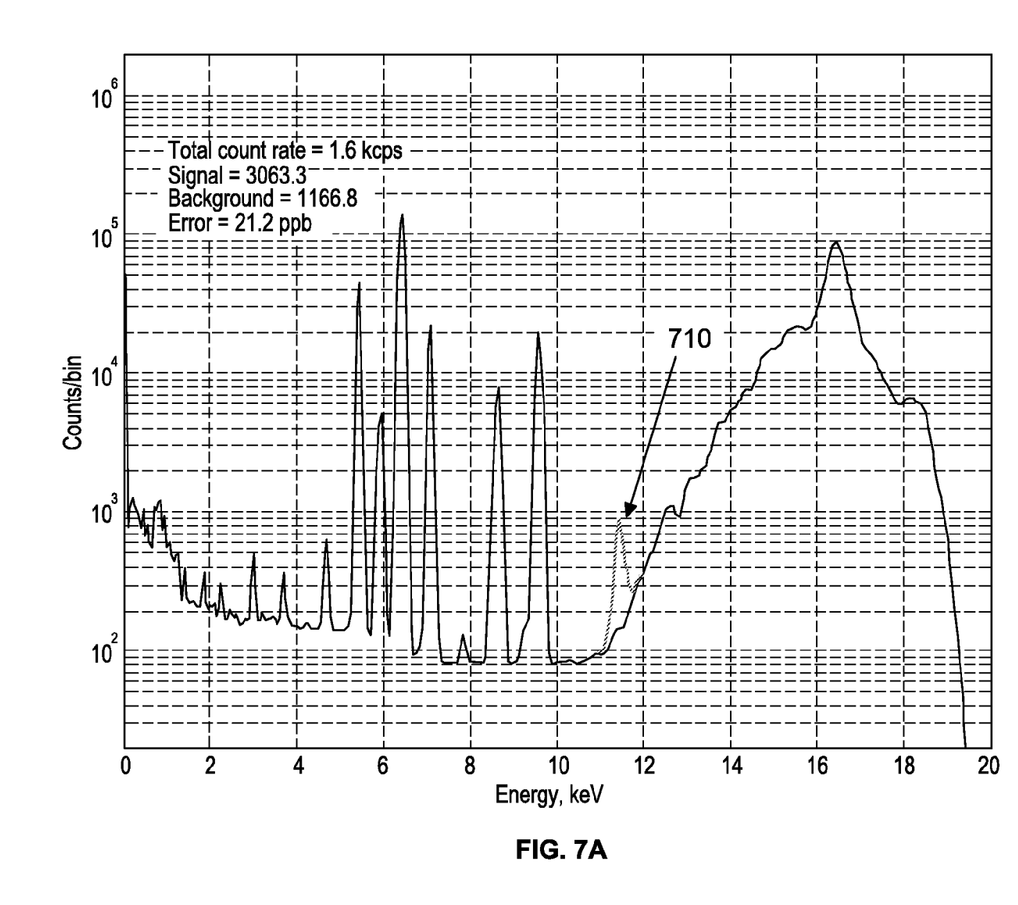
FIG. 7A is a graph showing simulated gold X-ray fluorescence spectra for an instrument constructed according to the specification herein.
Figure 7B:
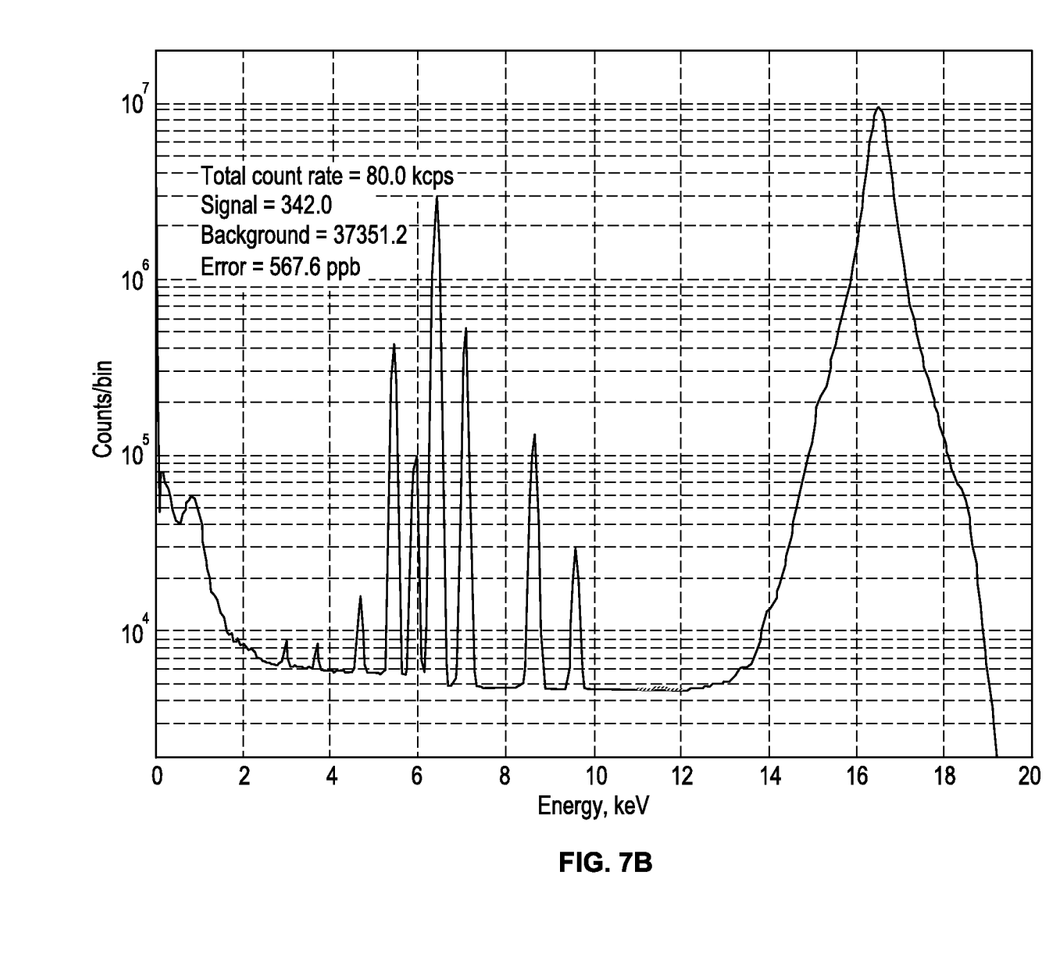
FIG. 7B is a graph showing simulated gold X-ray fluorescence spectra for a conventional spectrometer instrument.

To illustrate the advantages of an X-ray fluorescence analyser configured in accordance with the preceding directions, consider the results presented in FIGS. 7A and 7B. The two graphs show simulated X-ray spectra for a gold-ore slurry. The slurry composition is 25 wt % solids, 75 wt % water and the solid component contains 1 part-per-million gold.

In FIG. 7A, an X-ray fluorescence analyser configured with a two optical element arrangement described herein is used to irradiate the slurry with 17.4 keV X-rays emitted from a Mo-target X-ray tube and to focus the 11.4 keV gold fluorescent X-rays back on to the detector. The peak (710) indicates the signal from the gold fluorescence. The signal from the gold fluorescence is approximately 2.6 times larger than the background, and the calculated measurement error for a 30-minute measurement time is 21 parts-per-billion (0.021 parts per million).

In FIG. 7B, an optical element with a crystal component between the source and slurry is used to focus 17.4 keV X-rays onto the slurry, but the optical element between the slurry and detector has been removed. As such, this design is more similar to a conventional X-ray fluorescence analyser. As the gold fluorescence X-rays are no longer focused onto the detector, the fluorescence signal is reduced by approximately an order of magnitude. At the same time, the background levels under the gold peak are increased more than 30-fold, as X-rays scattered from the sample can now reach the detector. Together, these two effects increase the measurement error for a 30-minute measurement more than 25-fold to 0.57 parts-per-million.

Optimum performance is obtained when the portion of the log spiral used includes the point where the tangent to the curve is parallel to the axis. In other words, the radius of the curve in the centre is larger than the radii at either end. As currently technology only allows HOPG crystals to be made if the largest radius is at one end of the crystal, the inventors manufacture crystals in two halves which are then joined together after manufacture.

Advantageously, the angle between the axes of the two crystal components may be made less than 90°, or as small as possible. Angles less than 90° provide better matching of the irradiated area of the sample and the field of view of the second crystal optical element. Angles less than 90°, which lead to the a reduction in the angle that the axis of the second crystal optical element makes with the normal of the surface of the sample also serve to increase the proportion of fluorescent X-rays escaping in the direction of the detector without being absorbed in the sample. In a conventional X-ray fluorescence instrument, the source and detector are positioned to subtend an angle of 90° at the surface of the sample to minimise the number of inelastically scattered X-rays that reach the detector. The proposed design efficiently suppresses these inelastically scattered X-rays, allowing smaller source-detector angles to be used to advantage.

It is observed that the prior art tends to talk of the substrate being made in the form of a logarithmic spiral of revolution. However, because the HOPG crystals have a finite thickness, it has been observed that better results are obtained if the substrate is shaped so that the logarithmic spiral lies at the average reflection depth inside the crystal and not at the rear surface of the crystal.

The analyser is configurable to enable two or more detectors to be used, where the second focusing monochromators associated with the detectors are either identical or different. For example, using two detectors with identical monochromators doubles the count rate for trace elements, improving the measurement accuracy achievable in a given measurement time. Alternatively, two monochromators tuned to different X-ray energies could be used to detect fluorescent X-rays from different elements.

Figure 8:
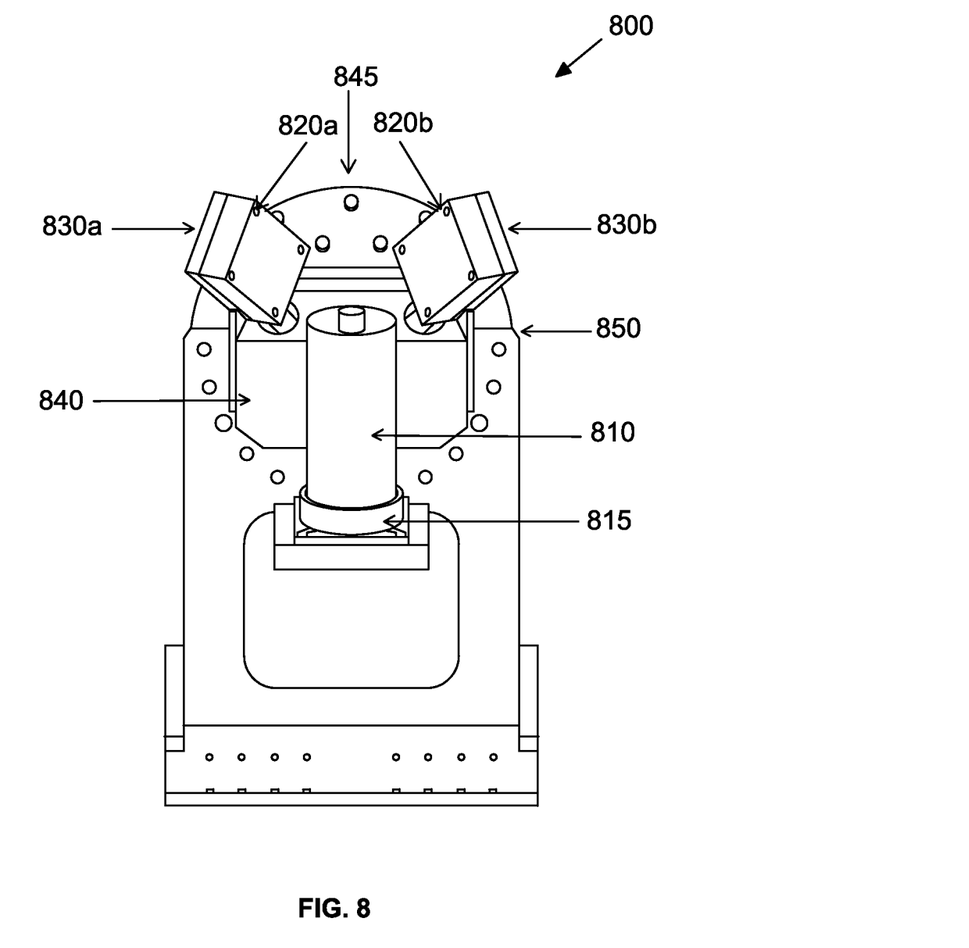
FIG. 8 is a view of an X-ray fluorescence analyser in accordance with a further embodiment of the invention.

FIG. 8 illustrates a view of an X-ray fluorescence analyser having a two detector arrangement. The components of the X-ray fluorescence analyser 800 which are visible are an X-ray tube 810, an X-ray tube bracket 815 which supports the X-ray tube, and a first and second energy resolving X-ray detector 820*a* and 820*b* each of which are supported by a detector bracket 830*a* and 830*b*. A collimator block 840 is provided to supporting a pair of outer collimating rings (not shown) each of which are situated in front of one of the energy resolving detectors 820*a*, 820*b*. The collimator block 840 is itself mounted to a collimator block bracket 845. The detector brackets 830*a*, 830*b* and collimator block bracket 845 are all carried on a mounting flange assembly 850. The X-ray tube bracket 815 is mounted to the 3D linear translation stages assembly (not shown) in order to align the tube with the crystal in the block.

The X-ray detectors are preferably small (approximately 3 to 8 mm diameter) silicon PIN or silicon drift detectors. The silicon drift detector uses a special electrode structure to guide the electrons to a very small, low capacitance anode. A key advantage of using a silicon drift detector is that they have much better energy resolution while operating at much higher count rates than conventional diodes of a comparable area.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The claims defining the invention are as follows:

1. An X-ray fluorescence analyser is provided comprising:
    an X-ray source selected to produce an intense X-ray beam;
    a first optical element that focuses the X-ray beam produced by the X-ray source onto a sample and selects X-rays of a desired energy;
    an energy resolving detector; and
    a second optical element that receives fluorescent X-rays emitted from elements in the sample and focuses a selected energy range of said fluorescent X-rays onto said energy resolving detector;
    wherein each of the first and second optical elements includes a crystal component, and wherein the X-ray fluorescence analyser is configured such that:
    (i) the X-ray source has a spot size dimensioned such that the spot size is substantially in a field of view of the first optical element, and
    (ii) the first optical element focuses the X-ray beam emitted by the X-ray source onto an area of the sample that corresponds to a field-of-view of the second optical element;
    wherein the respective field of view for the first and the second optical element is defined as an area in a source plane of the crystal component of the respective first or second optical element over which X-rays are able to be emitted and still efficiently be reflected by that respective first or second optical element.

2. The X-ray fluorescence analyser according to claim 1, wherein the X-ray source is selected to emit an intense X-ray beam from a region smaller than the field of view of the first optical element.

3. The X-ray fluorescence analyser according to claim 1, wherein X-ray source is selected to have a spot size having a diameter of <1 mm, preferably <0.5 mm, and more preferably <50 µm.

4. The X-ray fluorescence analyser according to claim 1, wherein the second optical element is configured to focus the selected energy range of said fluorescent X-rays onto an area that corresponds to the size of an active area of the energy resolving detector.

5. The X-ray fluorescence analyser according to claim 1, the crystal components of the first and second optical elements have the form of portion of a logarithmic spiral of revolution with a parametric form x=A cos $\theta e^{-b\theta}$, r =A sin $\theta e^{-b\theta}$;

wherein A and b are constants, x measures distance along the axis of revolution, r is the radius of the spiral and $\theta$ is the polar angle measured with respect to the axis of revolution.

6. The X-ray fluorescence analyser according to claim 5, wherein the parameters describing the shape of the logarithmic spiral for the second optical element are A, b, $x_1$ and $x_2$, where $x_1$ and $x_2$ are the limits of the portion of the logarithmic spiral forming the optical element, and wherein the values of these parameters are determined by the following steps:

(a) calculating A and b using equations $$\theta_b = \sin^{-1}\left(\frac{6.199}{E*d}\right),$$

$$b = \frac{1}{\tan\theta_b}$$

and $$A = \frac{\frac{1}{2}sf\exp(-b\theta_b)}{\cos(\theta_b)};$$

wherein s is an arbitrary focal shift parameter between 0 and 1, d is a lattice spacing of the crystal component, E is the energy of the fluorescent X-ray to be focused by the element and f is a desired focal length of the crystal component, equal to the distance from a surface of the sample to a surface of the detector;

(b) calculating the radius R in the focal plane of the X-ray beam focused by the crystal component using the equation R=|r−(f−x)tan(2$\theta_b$−$\theta$)|; and (c) identifying values $x_1$ and $x_2$ that correspond to the range of x values over which R is less than the radius of the X-ray detector.

7. The X-ray fluorescence analyser according to claim 6, wherein steps (a), (b) and (c) are repeated for different values of f and s to identify the design of the crystal component that subtends the largest solid angle at the sample, whilst simultaneously having the smallest size that can be physically manufactured.

8. The X-ray fluorescence analyser according to claim 1, wherein the field of view of the second optical element is estimated using a numerical integration or a stochastic estimation procedure.

9. The X-ray fluorescence analyser according to claim 1, wherein the crystal component of the first optical element is designed such that it produces a focal spot substantially matching the field of view of the second optical element.

10. The X-ray fluorescence analyser according to claim 9, wherein the crystal component of the first optical element has the form of a logarithmic spiral of revolution, wherein the form of the spiral is described by a separate set of parameters A, b, $x_1$ and $x_2$ which are determined by the following steps:

(a) calculating A and b using equations $$\theta_b = \sin^{-1}\left(\frac{6.199}{E*d}\right),$$

$$b = \frac{1}{\tan\theta_b}$$

and $$A = \frac{\frac{1}{2}sf\exp(-b\theta_b)}{\cos(\theta_b)};$$

where s is an arbitrary focal shift parameter between 0 and 1, d is a lattice spacing of the crystal, E is the characteristic X-ray energy emitted by the source that is to be focused by the optical element and f is the focal length of the crystal component, equal to the distance from the source emission point to the surface of the sample; and (b) calculating the radius R in the focal plane of the X-ray beam focused by the crystal component using the equation R=|r−(f−x)tan(2$\theta_b$−$\theta$)|, and (c) identifying values $x_1$ and $x_2$ that correspond to the range of x values over which R is less than the radius of field of view of the second optical element.

11. The X-ray fluorescence analyser according to claim 10, wherein steps (a), (b) and (c) are repeated for different values of f and s to identify the design of the crystal component that subtends the largest solid angle at the X-ray source emission point, whilst simultaneously having the smallest size that can be physically manufactured and positioned with respect to the X-ray source.

12. The X-ray fluorescence analyser according to claim 1, wherein each of the first and second optical elements comprise a machined metal or plastic substrate coated in the crystal component.

13. The X-ray fluorescence analyser according to claim 12, wherein the crystal component of the first and second optical elements comprises highly-oriented pyrolytic graphite.

14. The X-ray fluorescence analyser according to claim 1, further comprising a support structure to rigidly hold at least the first optical element, the second optical element and the energy resolving detector in relation to one another.

15. The X-ray fluorescence analyser according to claim 14, further comprising mounting means for mounting the X-ray source and bringing the X-ray source into correct alignment with the support structure.

16. The X-ray fluorescence analyser according to claim 15, wherein the mounting means comprises translation stages to provide at least tranverse motion in two axes and preferably 3-dimensional translation.

17. The X-ray fluorescence analyser according to claim 1, further comprising two or more energy resolving detectors each with an associated second optical element.

18. The X-ray fluorescence analyser according to claim 12, wherein the crystal component comprises a layer with a mosaic of individual crystals with slightly different orientations.

* * * * *